(12) United States Patent
Gehring

(10) Patent No.: US 8,756,981 B2
(45) Date of Patent: Jun. 24, 2014

(54) MEASUREMENT DEVICE WITH RESONATOR

(75) Inventor: Frank K. Gehring, Obernheim (DE)

(73) Assignee: Andreas Hettich GmbH & Co. KG, Tuttlingen (DE)

( * ) Notice: Subject to any disclaimer, the term of this patent is extended or adjusted under 35 U.S.C. 154(b) by 277 days.

(21) Appl. No.: 13/053,136

(22) Filed: Mar. 21, 2011

(65) Prior Publication Data

US 2011/0232374 A1      Sep. 29, 2011

(30) Foreign Application Priority Data

Mar. 23, 2010  (DE) .......................... 10 2010 016 103

(51) Int. Cl.
*G01N 29/00*          (2006.01)

(52) U.S. Cl.
USPC ........... 73/61.49; 73/61.79; 73/64.53; 73/579

(58) Field of Classification Search
USPC ............ 73/24.01, 24.03, 24.06, 61.45, 61.49, 73/61.57, 61.59, 64.53, 579, 61.79
See application file for complete search history.

(56) References Cited

U.S. PATENT DOCUMENTS

| | | | | |
|---|---|---|---|---|
| 5,217,595 A | * | 6/1993 | Smith et al. | 204/412 |
| 5,399,256 A | * | 3/1995 | Bohs et al. | 204/409 |
| 6,709,856 B2 | * | 3/2004 | Matsumoto et al. | 435/287.1 |
| 7,435,320 B2 | * | 10/2008 | Han et al. | 204/409 |
| 8,230,724 B2 | * | 7/2012 | Gehring | 73/61.49 |
| 8,268,146 B2 | * | 9/2012 | Jiang et al. | 204/409 |
| 2011/0283781 A1 | * | 11/2011 | Gehring | 73/64.53 |

FOREIGN PATENT DOCUMENTS

JP        2003-526780         9/2003

OTHER PUBLICATIONS

Japanese Patent Office, Office Action, pp. 1-2, Japanese Application No. 2011-063948, Jan. 28, 2014.
Japanese Patent Office, Partial Translation of the Office Action, p. 1, Japanese Application No. 2011-516712.

* cited by examiner

*Primary Examiner* — Hezron E Williams
*Assistant Examiner* — Hoang Nguyen
(74) *Attorney, Agent, or Firm* — Woodling, Krost and Rust

(57) ABSTRACT

The invention relates to a measurement device with at least one resonator, comprising a measurement chamber with a fluidic input and a fluidic output wherein the measurement chamber is delimited, at its bottom surface, by a resonator, and wherein the resonator surface is configured to be electrically conducting, and the resonator surface forms the working electrode for an electrochemical measurement, and wherein electrodes are provided at the fluidic input and/or output at the transition to the measurement chamber. The invention is characterized in that the electrodes are exchangeable and allow the reception of a fluidic connection.

11 Claims, 2 Drawing Sheets

MEASUREMENT DEVICE WITH RESONATOR

Figure 1:
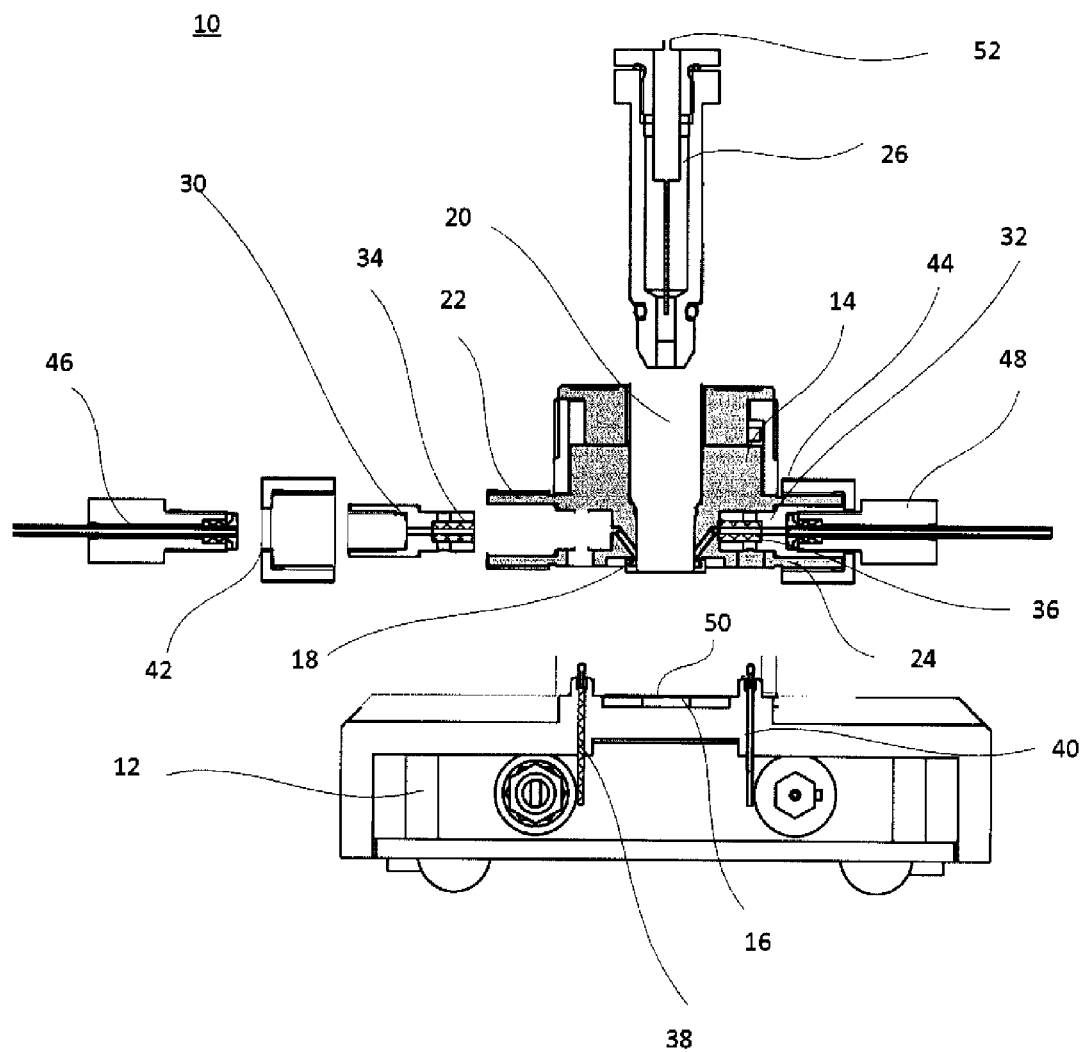

The invention relates to a measurement device with a resonator.

From DE 10 2006 015 512, measurement devices with an oscillating quartz as resonator are known in which the oscillating quartz is exchangeable. The measurement devices comprise measurement chambers through which a fluid can be passed through a fluidic input and output, respectively. Typically, the oscillation parameters of the oscillating quartz are measured on the basis of which measurement the characteristics of a fluid are determined.

It is furthermore known to use the oscillating quartz besides the typical measurements of the oscillation parameters also for electrochemical measurements. In general, basically three electrodes are provided for electrochemical measurements: a working electrode, a counter electrode and a reference electrode. For the use of the oscillating quartz measurement chamber for electrochemical measurements, it is required that the oscillating quartz acts as an electrode, and, additionally, at least one counter electrode is provided. According to the state of the art, the counter electrode is arranged in a measurement chamber in juxtaposition to the oscillating quartz.

For exactly determining the electrochemical characteristics of a fluid, a reference electrode may additional be provided at the fluidic inputs and outputs, according to the state of the art.

The systems according to the state of the art have the deficiency that the counter electrode is worn out during its usage. This has the consequence that the complete measurement chamber becomes unusable when the counter electrode is worn out.

The invention is based on the objective to provide a fluidic measurement device with a resonator which device enables an electrochemical measurement and ensures the long lasting usage of the measurement chamber.

In a matter known per se, a measurement device with a resonator for the analysis of oscillation parameters of a resonator comprises fluid connections, wherein the resonator may also be used as working electrode for electrochemical measurements. A fluidic system or a reservoir container may be connected to the fluidic connections of the measurement device by means of fluidic connection piece. Furthermore, at least one further counter electrode is provided in the measurement device which comprises a measurement chamber besides the oscillating quartz as working electrode.

According to the invention, the electrodes of the measurement device are configured to be exchangeable. At the one hand, this necessitates the exchangeability of the resonator of the measurement device, and, on the other hand, at least one further exchangeable electrode has to be provided. This may be a connection electrode which is exchangeable arranged in the fluidic connection area.

The exchangeable arrangement of the electrodes has the advantage that, after wear-out of the electrodes they can be exchanged as required in a simple manner without impairing the functionality of the measurement chamber. The fluidic inputs and outputs of the measurement chamber are arranged essentially in a horizontal plane, wherein the flow direction is of minor importance in general, since the measurement chamber according to the invention is arranged essentially symmetrically.

In a particularly advantageous embodiment, the electrode may be configured tubular and may, at least in part, form the fluid channel for the passage of the fluid. The configuration of the electrode as fluid channel has a particularly advantageous effect in connection with the use of the connection electrode as counter electrode since it comprises a particularly large electrode surface and, therefore, allows only a minor current density.

In an advantageous way, the electrode may be integrated into a bushing which is inserted into the fluidic connection. This facilitates the handling on exchanging the electrodes since the bushing may be structured essentially larger than the inserted electrode. The bushing may, preferably, be formed out of PEEK. Furthermore, the PEEK bushing may also be formed without an electrode which does not only allow the exchange of one worn out electrode, but also bushings without electrodes can be used. By using electrode-less and, thereby, lower cost bushings, a contamination of the electrodes can be avoided if measurements are to be carried out which do not necessitate the electrodes.

Furthermore, the bushing may be structured such that it can take up the fluid connection piece of the fluidic system to be connected or of the supply container and may mount it without leakage. In particular, the bushing is mounted to this fluidic connection by means of a locknut which engages an outer thread at the fluidic connection. This offers a simple and fast possibility to lock in place an inserted bushing in a fluid tight manner.

This allows a multifunctional usage of the measurement chamber into which the electrodes may be inserted if necessary especially for electrochemical measurements. For measurements in which no electrochemical analysis is required, the electrodes are, therefore, not put under load.

In case an inserted bushing is not used, the connection piece may be screwed directly into the fluidic input and output connections, respectively, in a further embodiment.

In particular, one counter electrode is provided at the fluidic input and output each. For example, a process control may carried out with this arrangement by means of an electrochemical measurement which is carried out by means of these electrodes in parallel to the oscillating quartz measurement. For example, differing signals between the input and output are resulting when an air bubble is asymmetricaly enclosed in the chamber.

If, for example, differing fluids are sequentially introduced into the measurement channel, mixed fluids are resulting the gradual concentration of which may be detected from the input to the output. Correspondingly, the electrical change which is influenced by the development of the change of concentration of the respective fluid with respect to the proceeding one, may be measured by means of the electrodes.

In a particularly advantageous embodiment, the measurement device is constructed in two parts. The oscillating quartz is located, in this embodiment, in between the upper and the lower part. The fluidic connections are integrated in the upper part. The upper and the lower part form, after being mounted, the measurement chamber wherein it is delimited downwards by means of the oscillating quartz. The upper and the lower part may be braced together by means of a bayonet connection. The arrangement of the electrical connections in the upper part has the advantage that an electrochemical measurement chamber according to the invention may be mounted onto a already available carrying unit (lower part) of the state of the art.

As an alternative to the electrical connections provided in the upper part, those may also be provided in the lower part. The electrodes in the measurement chamber, i.e. the electrodes sitting in the fluidic connections and also the reference electrodes, may be connected through the lower part of the measurement device. Contacting through the lower part has the advantage that the operation of the measurement chamber is simplified since no connection cables are connected to the upper and, thereby, potentially removable part.

The contact between the connection portion and the electrodes is made as soon as the upper part is connected to the lower part. In particular, such contacts are formed as pins and spring pins, respectively.

When the upper part is positioned onto the lower part, the spring pins press against the connection electrodes.

Furthermore, a valve opening may be provided in the upper part which opening is positioned vertically above the resonator and which allows the insertion of a stem wherein the lower stem surface then forms the upper delimitation of the measurement chamber. In an advantageous way, it can also be configured to be transparent which allows observation of the processes.

Advantageously, also an electrode stem may be inserted into the opening instead of the transparent stem. The electrode stem forms preferable the reference electrode. The variable insertion of the electrode stem into the vertical opening of the measurement device has the advantage that it is accessible and allows adaption to different reference electrodes for different process fluids. For example, an Ag/AgCl or a Pt/NaCl reference electrode may be inserted. The reference electrode is adapted in its edge area such that it allows a flow through the measurement chamber as undisturbed as possible.

In particular, the electrode stem is located between the fluidic channels of the fluidic inputs and outputs. The electrode stem is adapted in its shape at the transition to the fluidic channels in order to allow a flow as undisturbed as possible and in order not to generate dead volumes in the transition area between the fluidic connections and the measurement chamber.

A further advantage on the basis of the exchangeability of the reference electrode is resulting thereby that the reference electrode may comprise, at its end facing the measurement chamber, a glass drip which has to kept continuously in moisture since it becomes porous and accordingly unusable otherwise. By means of the removability of the reference electrode, the measurement device must not necessarily be kept in a moist environment, but the reference electrode can be separately removed and stored in a moist or wet environment independently from the measurement device.

In a particularly advantageous way, the counter electrodes may be formed out of platinum. Platinum is inert and correspondingly biocompatible thereby multiple fluids may be used.

Furthermore, a heating-cooling-element may be arranged in the lower part whereby the measurement chamber may be temperature controlled. The oscillating quartz has two contacts which are arranged at the bottom side of the oscillating quartz and are connected to the connecting positions at the lower part of the measurement device. Thereby, the measurement device offers interfaces for signal input and data input, respectively, as well as for the excitation of the oscillating quartz.

If the oscillating quartz is glued to a foil at its measurement surface, it can be sealed free of tension.

In a further advantageous embodiment, a liquid receiving device may be connected to the connection portion. The liquid take-up device allows a hydrostatic measurement as soon as the liquid take-up devices are filled with the sample fluid.

In the following, the invention is explained in more detail with reference to the drawing. Herein, further features and advantages of the invention become apparent from the drawing and the description thereof. In the drawings, the reference signs are used which are listed in the reference sign list.

Figure 2:
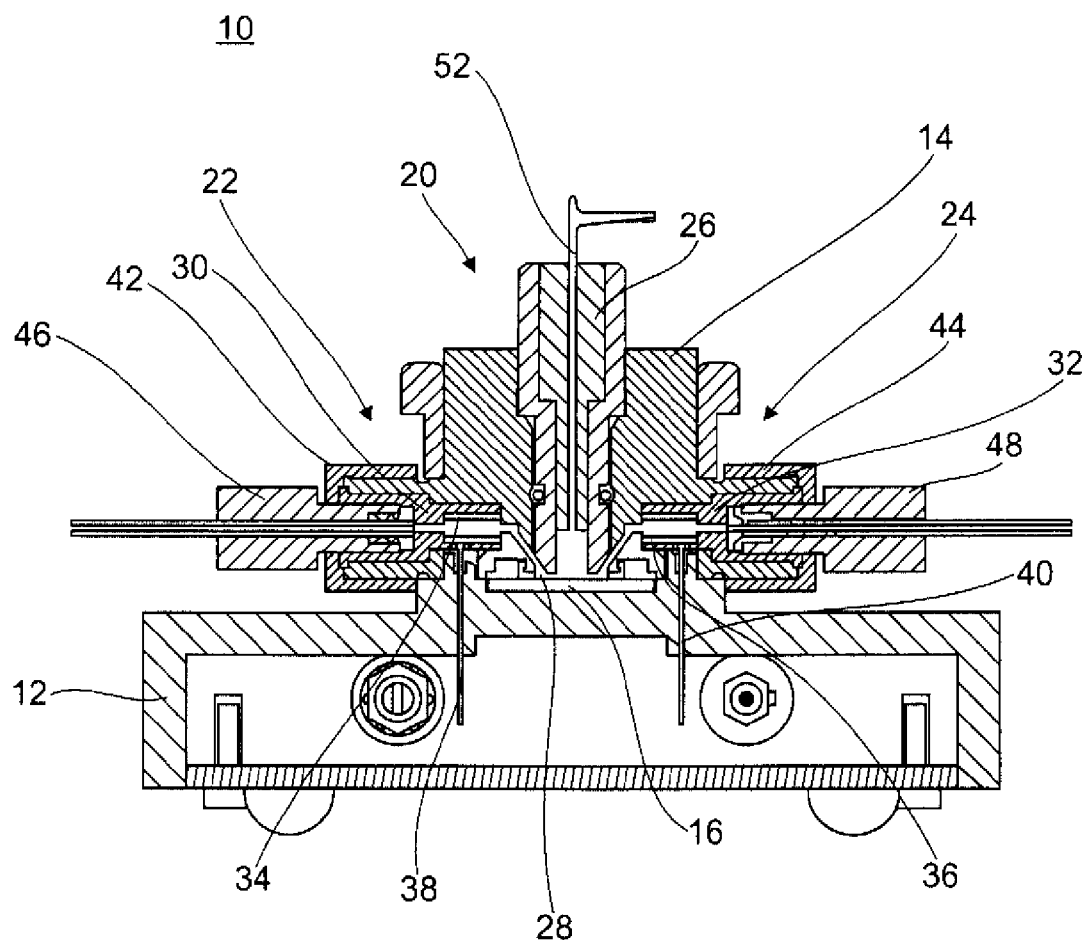

In the drawings:

FIG. 1 is a section through a measurement chamber according to an embodiment of the invention; and FIG. 2 is an assembled oscillating quartz measurement chamber.

FIG. 1 shows a measurement device 10 in section. The measurement device 10 comprises a lower part 12 and an upper part 14. The upper part 14 is fixed to the lower part 12 by means of a bayonet connection. By means of the connection of the upper part 14 and the lower part 12, an oscillating quartz 16 inserted into the lower part is fixed. At the transition between the upper part 14 and the oscillating quartz 16, a sealing 18 is provided which delimits the measurement chamber 28 to the side. The upper part 14 comprises additionally an opening 20 in vertical direction as well as a connection portion 22 and 24 in a horizontal direction. The connection portions 22, 24 in a horizontal direction essentially serve for the fluidic inflow and drainage flow of the measurement chamber. The opening 20 receives a closure plug or a reference electrode 26 which limits the measurement chamber.

In the sense of the invention, bushings 30, 32 are received in the connection portions 22, 24. Electrodes 34, 36 are integrated into the bushings 30, 32 at a forward end thereof. These electrodes are formed tubular and form the fluid channel in the front part of the bushings 30, 32. The electrodes 34, 36 are provided for an electrochemical measurement as counter electrodes. For contacting these electrodes 34, 36, spring pins are integrated into the lower part 12 which pins contact the electrodes 34, 36 through a recess in the bushing 30, 32 upon closing of the bayonet connection. The spring pins 38, 40 are connected to connections at the housing by means of electrical conductors. This allows a simple voltage tapping at the counter electrodes 34, 36.

The bushings 30, 32 are fluid-tightly coupled to the measurement chamber by means of locknuts 42, 44 which engage an outer thread at the connection portions 22, 24. Furthermore, the bushings 30, 32 comprise an inner thread corresponding to the one of the connection portions 46, 48. The connection portions 46, 48 are screwed into the bushings 30, 32 and, thereby, provide the connection for the liquid supply.

The surface of the oscillating quartz 16 is provided with an electrically conducting layer 50. This is preferably formed out of platinum. By means of this layer, the oscillating quartz forms the working electrode for the electrochemical measurement.

The reference electrode 26 is inserted into the opening 20 of the upper part 15 and is formed as reference electrode. The reference electrode comprises a conductor 52 which is inserted into a saline solution. The saline solution is separated from the measurement chamber by means of a semi permeable membrane.

This arrangement has the advantage that the reference electrode as well as the counter electrode 34, 36 may be exchanged with their bushings 30, 32 as soon as those are worn out. This is possible in a simple way when the locknut 42, 44 is removed from the connection portion 22, 24. The hushing can then simply be removed and exchanged with a new one. Accordingly, the complete measurement chamber has not to be exchanged just because the counter electrode has worn out.

FIG. 2 shows the oscillating quartz measurement chamber 10 in a closed state. In this embodiment, the oscillating quartz forms the lower side of the measurement chamber 28 whereas the reference electrode 26 upwards delimits the measurement chamber 28 with its membrane. The measurement space is delimited by the sealing ring 18 to the side. The spring pins 38, 40 contact the counter electrodes 34, 36 in the bushings as soon as the upper part and the lower part 12, 14 are put together.

LIST OF REFERENCE SIGNS 12 lower part
14 upper part
16 oscillating quartz
18 sealing ring
20 vertical opening
22 horizontal connection portion
24 vertical connection portion
26 reference electrode
28 measurement chamber
30 bushing
32 bushing
34 counter electrode
36 counter electrode
38 spring pin
40 spring pin
42 locknut
44 locknut
46 connection portion
48 connection portion
50 metal layer

The invention claimed is:

1. Measurement device with at least one resonator; comprising:
   an upper part and a lower part;
   said upper and lower parts joined together at a transition;
   a measurement chamber;
   said measurement chamber includes a fluidic input connection and a fluidic output connection;
   said fluidic input connection includes an input electrode and said fluidic output connection includes an output electrode;
   said input electrode is tubularly shaped;
   said input electrode includes a fluidic channel for the fluid to be measured;
   said output electrode is tubularly shaped;
   said output electrode includes a fluidic channel for the fluid to be measured;
   said measurement chamber is delimited by a resonator;
   said resonator includes a surface;
   said surface of said resonator contacts fluid to be measured and is electrically conductive, said surface of said resonator is a working electrode for an electrochemical measurement;
   said working electrode, said input electrode and said output electrode are exchangeable; and,
   said electrodes reside in proximity to said upper and lower parts.

2. Measurement device according to claim 1, wherein:
   said input and output counter electrodes are each arranged in a bushing which allows insertion of a fluid connection piece.

3. Measurement device according to claim 2, wherein said bushings are adapted to be fixed to said fluidic connections by a locknut.

4. Measurement device according to claim 1, further comprising:
   a vertical opening, said vertical opening spaced apart from said resonator;
   a reference electrode;
   said reference electrode resides in said vertical opening, said reference electrode delimits said measurement chamber.

5. Measurement device according to claim 1, further comprising:
   said upper part is removable;
   said lower part includes electrical first and second electrical contacts;
   said tubularly shaped input electrode is a counter electrode and said tubularlarly shaped output electrode is a counter electrode; and
   said first and second electrical contacts interengage said input counter electrode and said output counter electrode, respectively.

6. Measurement device according to claim 5, wherein said first and second electrical contacts are spring pins.

7. Measurement device according to claim 5, wherein said first and second electrical contacts engage said input and output counter electrodes when the upper removable part and the lower part are assembled together.

8. Measurement device according to claim 1, wherein said lower part includes a device for a temperature control of said measurement chamber.

9. Measurement device according to claim 1, further comprising:
   a reference electrode, and, said reference electrode being exchangeable.

10. Measurement device with at least one resonator; comprising:
    an upper part and a lower part;
    said upper and lower parts joined together at a transition;
    a measurement chamber;
    said measurement chamber includes a fluidic input connection and a fluidic output connection;
    said fluidic input connection includes an input counter electrode and said fluidic output connection includes an output counter electrode;
    said measurement chamber is delimited by a resonator;
    said resonator includes a surface;
    said surface of said resonator contacts fluid to be measured and is electrically conductive, said surface of said resonator is a working electrode for an electrochemical measurement;
    said working electrode, said input counter electrode and said output counter electrode are exchangeable; and
    said electrodes reside in proximity to said upper and lower parts.

11. Measurement device according to claim 10, further comprising: a reference electrode, and, said reference electrode being exchangeable.

* * * * *

UNITED STATES PATENT AND TRADEMARK OFFICE
CERTIFICATE OF CORRECTION

PATENT NO. : 8,756,981 B2  
APPLICATION NO. : 13/053136  
DATED : June 24, 2014  
INVENTOR(S) : Gehring Page 1 of 1

It is certified that error appears in the above-identified patent and that said Letters Patent is hereby corrected as shown below:

In the Specification

Col. 4, line 59, before "can" delete "hushing" and insert --bushing-- therefor.

Col. 6, line 30, after "device for" delete "a".

Signed and Sealed this  
Seventh Day of October, 2014

Michelle K. Lee  
*Deputy Director of the United States Patent and Trademark Office*